US008109271B2

(12) United States Patent  
Vandine

(10) Patent No.: US 8,109,271 B2  
(45) Date of Patent: Feb. 7, 2012

(54) METHOD AND APPARATUS FOR SECURING A PATIENT INTERFACE TO A PATIENT'S FACE

(75) Inventor: Joseph Douglas Vandine, Newark, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1063 days.

(21) Appl. No.: 11/470,832

(22) Filed: Sep. 7, 2006

(65) Prior Publication Data

US 2008/0060654 A1 Mar. 13, 2008

(51) Int. Cl.  
*A62B 18/08* (2006.01)

(52) U.S. Cl. .................................. 128/207.11

(58) Field of Classification Search ............ 128/207.11, 128/206.27, 206.21, 206.28, 207.13, 205.25, 128/206.12, 206.13; 2/209.7, 9, 206, 174, 2/202  
See application file for complete search history.

(56) References Cited

U.S. PATENT DOCUMENTS

| | | | | |
|---|---|---|---|---|
| 695,403 | A * | 3/1902 | Longden | 128/206.12 |
| 718,785 | A * | 1/1903 | McNary | 128/207.18 |
| 891,122 | A * | 6/1908 | Wilcox | 2/206 |
| 1,023,677 | A * | 4/1912 | Pass | 2/173 |
| 3,271,781 | A * | 9/1966 | Sontag et al. | 2/202 |
| 4,610,247 | A * | 9/1986 | Stroup | 128/201.28 |
| 4,825,473 | A * | 5/1989 | Brame | 2/202 |
| 4,915,106 | A | 4/1990 | Aulgur et al. | 128/207.11 |
| 4,972,520 | A * | 11/1990 | Grilliot et al. | 2/5 |
| 5,036,846 | A | 8/1991 | Aulgur et al. | 128/207.11 |
| 5,038,776 | A | 8/1991 | Harrison et al. | 128/207.11 |
| 5,069,205 | A | 12/1991 | Urso | 128/201.24 |
| 5,181,507 | A | 1/1993 | Michel et al. | 128/201.25 |
| 5,269,296 | A | 12/1993 | Landis | 128/207.18 |
| 5,370,110 | A * | 12/1994 | Corn | 128/201.22 |
| 5,429,126 | A | 7/1995 | Bracken | 128/207.11 |
| 5,441,046 | A | 8/1995 | Starr et al. | 128/207.11 |
| 5,503,147 | A | 4/1996 | Bertheau | 128/207.11 |
| 5,517,986 | A | 5/1996 | Starr et al. | 128/206.24 |
| 5,623,923 | A | 4/1997 | Bertheau et al. | 128/207.11 |
| 5,662,101 | A | 9/1997 | Ogden et al. | 128/205.25 |
| 5,697,363 | A | 12/1997 | Hart | 128/201.24 |
| 5,724,965 | A | 3/1998 | Handke et al. | 128/207.13 |
| 5,941,245 | A | 8/1999 | Hannah et al. | 128/207.11 |
| 6,039,045 | A | 3/2000 | Bertheau et al. | 128/207.11 |
| 6,044,844 | A | 4/2000 | Kwok et al. | 128/207.11 |
| 6,119,694 | A | 9/2000 | Correa et al. | 128/207.13 |
| 6,123,071 | A | 9/2000 | Berthon-Jones et al. | 128/204.18 |
| 6,131,203 | A * | 10/2000 | Cominsky | 2/202 |
| 6,182,298 | B1 | 2/2001 | Dampney | 2/422 |
| 6,192,886 | B1 | 2/2001 | Rudolph | 128/207.13 |
| 6,272,690 | B1 * | 8/2001 | Carey et al. | 2/206 |
| 6,338,342 | B1 | 1/2002 | Fecteau et al. | 128/207.11 |
| 6,347,631 | B1 | 2/2002 | Hansen et al. | 128/207.11 |
| 6,374,826 | B1 | 4/2002 | Gunaratnam et al. | 128/206.27 |
| 6,386,198 | B1 | 5/2002 | Rugless | 128/206.21 |
| 6,470,886 | B1 | 10/2002 | Jestrabek-Hart | 128/207.11 |
| 6,494,207 | B1 | 12/2002 | Kwok | 128/207.11 |
| 6,497,232 | B2 | 12/2002 | Fecteau et al. | 128/207.11 |

(Continued)

*Primary Examiner* — Kristen Matter

(57) ABSTRACT

A breathing assistance system may include a patient interface configured to interface with a patient to communicate gas received from a gas delivery apparatus to the patient, and a securing system configured to secure the patient interface against the patient's face. The securing system may include one or more walls forming a generally tubular structure open at least at one end. At least a portion of the one or more walls may be elastic such that at least a portion of the generally tubular structure can be stretched over the patient's head.

13 Claims, 4 Drawing Sheets

U.S. PATENT DOCUMENTS

| | | | |
|---|---|---|---|
| 6,505,623 B1 | 1/2003 | Hansen | 128/207.11 |
| 6,513,526 B2 * | 2/2003 | Kwok et al. | 128/206.24 |
| 6,516,802 B2 | 2/2003 | Hansen et al. | 128/207.11 |
| 6,536,435 B1 | 3/2003 | Fecteau et al. | 128/207.11 |
| 6,571,797 B1 | 6/2003 | Magidson et al. | 128/205.27 |
| 6,588,424 B2 * | 7/2003 | Bardel | 128/207.11 |
| 6,615,834 B2 | 9/2003 | Gradon et al. | 128/207.11 |
| 6,619,288 B2 | 9/2003 | Demers et al. | 128/205.25 |
| 6,629,532 B2 | 10/2003 | Campbell, Sr. | 128/207.11 |
| 6,701,926 B2 | 3/2004 | Olsen et al. | 128/207.11 |
| 6,729,333 B2 | 5/2004 | Barnett et al. | 128/207.13 |
| 6,732,733 B1 | 5/2004 | Brostrom et al. | 128/206.27 |
| 6,745,772 B1 | 6/2004 | McLeod | 128/206.21 |
| 6,776,161 B2 | 8/2004 | Horn | 128/207.11 |
| 6,789,541 B2 | 9/2004 | Olsen et al. | 128/207.11 |
| 6,805,117 B1 | 10/2004 | Ho et al. | 128/201.22 |
| 6,854,465 B2 | 2/2005 | Bordewick et al. | 128/207.11 |
| 6,883,519 B2 | 4/2005 | Schmidtke et al. | 128/207.11 |
| 6,886,564 B2 | 5/2005 | Sullivan et al. | 128/206.24 |
| 6,907,882 B2 | 6/2005 | Ging et al. | 128/207.11 |
| 6,926,004 B2 | 8/2005 | Schumacher | 128/206.27 |
| 6,926,007 B2 | 8/2005 | Frank | 128/846 |
| 6,959,710 B2 | 11/2005 | Barnett et al. | 128/207.13 |
| 6,981,503 B1 | 1/2006 | Shapiro | 128/845 |
| 7,017,576 B2 | 3/2006 | Olsen et al. | 128/205.25 |
| 7,017,579 B2 | 3/2006 | Palmer | 128/207.17 |
| 7,036,508 B2 | 5/2006 | Kwok | 128/207.11 |
| 7,047,971 B2 | 5/2006 | Ho et al. | 128/207.11 |
| 7,047,972 B2 | 5/2006 | Ging et al. | 128/207.11 |
| 7,066,179 B2 | 6/2006 | Eaton et al. | 128/206.27 |
| 7,089,941 B2 | 8/2006 | Bordewick et al. | 128/207.11 |
| 7,096,867 B2 | 8/2006 | Smith et al. | 128/207.11 |
| 7,188,620 B2 | 3/2007 | Amarasinghe | 128/201.22 |
| 7,201,169 B2 | 4/2007 | Wilkie et al. | 128/207.18 |
| 7,225,811 B2 * | 6/2007 | Ruiz et al. | 128/207.11 |
| 7,231,921 B2 | 6/2007 | Palmer | 128/207.17 |
| 7,296,570 B2 * | 11/2007 | Hutchinson | 128/201.26 |
| 7,331,363 B2 * | 2/2008 | Lanzi | 139/422 |
| 2002/0096173 A1 * | 7/2002 | Berthon-Jones et al. | 128/204.23 |
| 2002/0096176 A1 | 7/2002 | Gunaratnam et al. | 128/207.11 |
| 2002/0189616 A1 | 12/2002 | Wolf | 128/205.25 |
| 2003/0051732 A1 | 3/2003 | Smith et al. | 128/206.27 |
| 2003/0084903 A1 | 5/2003 | Fecteau et al. | 128/206.27 |
| 2003/0196655 A1 | 10/2003 | Ging et al. | 128/201.22 |
| 2004/0025882 A1 | 2/2004 | Madaus et al. | 128/206.27 |
| 2004/0065328 A1 | 4/2004 | Amarasinghe et al. | 128/206.27 |
| 2004/0083534 A1 | 5/2004 | Ruiz et al. | 2/171.2 |
| 2004/0112377 A1 | 6/2004 | Amarasinghe et al. | 128/201.22 |
| 2004/0112384 A1 | 6/2004 | Lithgow et al. | 128/206.21 |
| 2004/0182398 A1 | 9/2004 | Sprinkle et al. | 128/207.13 |
| 2004/0221850 A1 | 11/2004 | Ging et al. | 128/206.27 |
| 2004/0226566 A1 | 11/2004 | Gunaratnam et al. | 128/207.18 |
| 2005/0051171 A1 | 3/2005 | Booth | 128/206.18 |
| 2005/0076913 A1 | 4/2005 | Ho et al. | 128/206.27 |
| 2005/0081858 A1 | 4/2005 | Raje et al. | 128/206.21 |
| 2005/0155604 A1 | 7/2005 | Ging et al. | 128/206.21 |
| 2005/0205096 A1 | 9/2005 | Matula, Jr. et al. | 128/207.11 |
| 2005/0279367 A1 | 12/2005 | Klemperer | 128/861 |
| 2005/0284481 A1 | 12/2005 | Meyer et al. | 128/207.11 |
| 2006/0000476 A1 | 1/2006 | Salem | 128/206.21 |
| 2006/0027236 A1 | 2/2006 | Barnett et al. | 128/206.24 |
| 2006/0032504 A1 | 2/2006 | Burton et al. | 128/207.11 |
| 2006/0042629 A1 | 3/2006 | Geist | 128/206.24 |
| 2006/0060200 A1 | 3/2006 | Ho et al. | 128/206.24 |
| 2006/0076019 A1 | 4/2006 | Ho | 128/206.24 |
| 2006/0090760 A1 | 5/2006 | Gradon et al. | 128/206.27 |
| 2006/0112961 A1 | 6/2006 | Aly | 128/206.11 |
| 2006/0118117 A1 | 6/2006 | Berthon-Jones et al. | 128/206.21 |
| 2006/0118119 A1 | 6/2006 | Berthon-Jones et al. | 128/207.11 |
| 2006/0162729 A1 | 7/2006 | Ging et al. | 128/206.27 |
| 2006/0174892 A1 | 8/2006 | Leksutin et al. | 128/207.11 |
| 2006/0191539 A1 | 8/2006 | Ho et al. | 128/207.11 |
| 2006/0207600 A1 | 9/2006 | Burrow et al. | 128/207.11 |
| 2006/0213521 A1 | 9/2006 | Radney | 128/207.11 |
| 2006/0225740 A1 | 10/2006 | Eaton et al. | 128/206.24 |
| 2006/0231102 A1 | 10/2006 | Bordewick et al. | 128/207.11 |
| 2006/0231103 A1 | 10/2006 | Matula, Jr. et al. | 128/207.13 |
| 2006/0272646 A1 | 12/2006 | Ho et al. | 128/207.11 |
| 2006/0283456 A1 * | 12/2006 | Geiselhart et al. | 128/206.24 |
| 2006/0283458 A1 | 12/2006 | Woodard et al. | 128/206.24 |
| 2006/0283460 A1 | 12/2006 | Brown et al. | 128/206.24 |
| 2006/0283461 A1 | 12/2006 | Lubke et al. | 128/207.11 |
| 2007/0017525 A1 | 1/2007 | Madaus et al. | 128/207.11 |
| 2007/0028919 A1 | 2/2007 | Ho | 128/204.18 |
| 2007/0044797 A1 | 3/2007 | Ho | 128/204.18 |
| 2007/0062539 A1 | 3/2007 | Gunaratnam et al. | 128/207.18 |
| 2007/0107723 A1 | 5/2007 | Berg | 128/200.26 |

* cited by examiner

METHOD AND APPARATUS FOR SECURING A PATIENT INTERFACE TO A PATIENT'S FACE

TECHNICAL FIELD

The present disclosure relates generally to the field of breathing assistance systems, e.g., a method and apparatus for securing a patient interface to a patient's face.

BACKGROUND

Obstructive Sleep Apnea (OSA) is a disorder in which the sufferer is unable to maintain patency of the upper airway while sleeping. The cause is typically a decrease in muscle tone in the tissues of the throat, although the condition can also be triggered or aggravated by being overweight. Symptoms of OSA may include impaired ability to concentrate during waking hours, memory loss, narcolepsy and, if untreated for a long time, heart disease emanating from repetitive, transient hypoxias and increased pulmonary vascular resistance.

In recent years, continuous positive airway pressure (CPAP) therapy has become a common prescription for individuals suffering from OSA and/or other breathing ailments. Such therapy may involve placement of a nose, mouth, or face mask on the patient during sleeping, while positive pressure air is continuously delivered to the patient through the mask. The positive pressure air may be delivered to the patient's upper airway to prevent the upper airway tissues from collapsing during sleep, thus reducing the occurrence and/or severity of OSA.

SUMMARY

According to one embodiment of the present disclosure, a breathing assistance system may include a patient interface configured to interface with a patient to communicate gas received from a gas delivery apparatus to the patient, and a securing system configured to secure the patient interface against the patient's face. The securing system may include one or more walls forming a generally tubular structure open at least at one end. At least a portion of the one or more walls may be elastic such that at least a portion of the generally tubular structure can be stretched over the patient's head.

According to another embodiment of the present disclosure, a method for securing a patient interface to a patient may be provided. A patient interface may be positioned relative to at least one of the nose and mouth of a patient. The patient interface may be configured to communicate gas received from a gas delivery apparatus to the patient. A securing system may be stretched over a substantial portion of the patient's head and at least a portion of the patient interface to secure the patient interface to the patient's face.

According to another embodiment of the present disclosure, a securing system for securing a patient interface to a patient's face may include a generally tubular structure open at least at one end, wherein at least a portion of the generally tubular structure is elastic such that at least a portion of the generally tubular structure can be stretched over the patient's head.

According to another embodiment of the present disclosure, a breathing assistance system may include a gas delivery apparatus, a mask apparatus in fluid communication with the gas delivery apparatus, and a securing system. The mask apparatus may include a patient interface configured to interface with a patient to communicate gas received from the gas delivery apparatus to the patient. The securing system may be configured to secure the patient interface against the patient's face. The securing system may include one or more walls forming a generally tubular structure open at least at one end. At least a portion of the one or more walls may be elastic such that at least a portion of the generally tubular structure can be stretched over the patient's head.

According to another embodiment of the present disclosure, a breathing assistance system may include gas delivery means for delivering gas toward a patient, patient interfacing means for communicating gas from the gas delivery means to the patient, and securing means for securing the patient interfacing means against a patient's face. The securing means may include one or more walls forming a generally tubular structure open at least at one end. At least a portion of the one or more walls may be elastic such that at least a portion of the generally tubular structure can be stretched over the patient's head.

DETAILED DESCRIPTION OF THE DRAWING

Selected embodiments of the disclosure may be understood by reference, in part, to FIGS. 1-7, wherein like numbers refer to same and like parts. The present disclosure relates generally to methods and apparatuses for securing a patient interface (e.g., a mask or nasal pillows) of a breathing assistance system (e.g., a ventilator, CPAP device, or BiPAP device, etc.) to a patient's face. In some embodiments, a tubular, elastic mesh or netting may be designed to fit over both the patient's head and the patient interface in order to secure the patient interface against the patient's face. In some embodiments, the pressure on the patient interface is relatively evenly distributed and/or does not significantly vary with patient sleeping position. The term "patient" may refer to any person or animal that may receive breathing assistance from any breathing assistance system, regardless of the medical status, official patient status, physical location, or any other characteristic of the person. Thus, for example, patients may include persons under official medical care (e.g., hospital patients), persons not under official medical care, persons receiving care at a medical care facility, persons receiving home care, etc.

Figure 1:
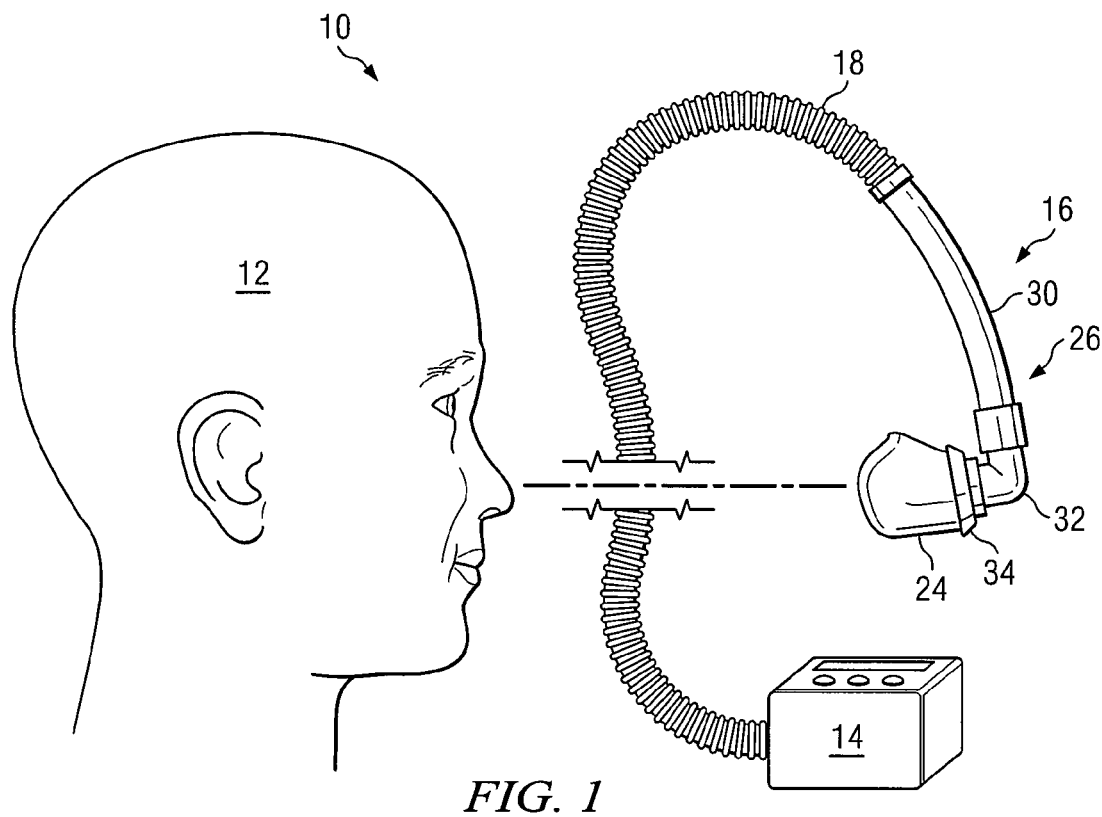
FIG. 1 illustrates a side view of a gas delivery apparatus and a patient, according to one embodiment of the disclosure.

FIG. 1 illustrates an example breathing assistance system 10, according to one embodiment of the disclosure. Breathing assistance system 10 may be generally configured to provide breathing assistance (e.g., providing ventilation and/or treating an apnea or other breathing condition) to a patient 12. Breathing assistance system 10 may include a gas delivery apparatus 14, a mask apparatus 16, a connection system 18, and a securing system 20.

Gas delivery apparatus 14 may include any device or devices configured to generate, supply, and/or deliver gas (e.g., pressurized air) toward patient 12 via mask apparatus 16. For example, gas delivery apparatus 14 may comprise a device capable of generating pressurized air (e.g., a ventilator, CPAP system, or BiPAP system), a wall outlet through which pressurized air may be supplied (e.g., in a hospital or clinic), one or more tanks of compressed gas, a compressor, or any other suitable source of pressurized or non-pressurized gas (not shown in figures). As used herein, the term "gas" may refer to any one or more gases and/or vaporized substances suitable to be delivered to and/or from a patient via one or more breathing orifices (e.g., the nose and/or mouth), such as air, nitrogen, oxygen, any other component of air, $CO_2$, vaporized water, vaporized medicines, and/or any combination of two or more of the above, for example.

Connection system 18 may include any device or devices for delivering gas from gas delivery apparatus 14 to mask apparatus 16. In some embodiments, connection system 18 may include one or more conduits (e.g., flexible hoses) and/or connectors coupled between gas delivery apparatus 14 and mask apparatus 16.

Mask apparatus 16 may comprise any suitable device or devices configured to interface with patient 12 to deliver gas from gas delivery apparatus 14 to patient 12. In some embodiments, mask apparatus 16 may include a patient interface 24 and one or more conduits 26 configured to deliver gas received from connection system 18 to patient interface 24. In an example embodiment, conduits 26 include a ventilation tube 30 that may be connected to an elbow 32. Elbow 32 may be connected to an interface coupler 34 configured to couple elbow 32 to patient interface 24. Connection system 18 may be coupled to ventilation tube 30 to deliver gas to patient 12 through ventilation tube 30, elbow 32, interface coupler 34 and patient interface 24. In alternative embodiments, certain ones of ventilation tube 30, elbow 32, interface coupler 34 and/or patient interface 24 may be integrated as a single component or may include multiple components.

Patient interface 24 may include any device for interfacing with a patient's face, such as a mask or cushion (e.g., a nasal cushion, a mouth cushion, or a full-face cushion) or nasal pillows, for example. Patient interface 24 may be connected to interface coupler 34 by clips, mated threads, an interference fit, a flange/recess configuration, or any other known or suitable means. Patient interface 24 may fit over the patient's nose and/or mouth, depending on the application. Patient interface 24 may also or alternatively be inserted into the nose and/or mouth of patient 12. Patient interface 24 may have any suitable shape and/or size to properly fit patient 12. In addition, patient interface 24 may be a single, integrated component, or may include multiple components coupled together.

In some embodiments, patient interface 24 may be made of any suitable resilient material suitable to provide a comfortable fit against the patient's face. For example, all or portions of patient interface 24 may be formed from one or more flexible or deformable materials, e.g., deformable polymers, plastic, rubber, silicon, or gel. In particular, at least portions of patient interface 24 in contact with the patient's face may be formed from a flexible or deformable material to provide an effective and comfortable seal against the face. In addition, a portion of patient interface 24 connected to interface coupler 34 may be formed from a flexible or deformable material that may be manipulated to mate with interface coupler 34 to releasably couple patient interface 24 to interface coupler 34.

Securing system 20 may be configured to secure patient interface 16 in position against the patient's face. Referring to the example embodiment shown in FIG. 2, securing system 20 may be a generally tubular-shaped structure having openings 38 at one or both ends. Securing system 20 may include one or more walls 40 formed from elastic filaments 42 arranged in a criss-cross pattern forming a mesh or net having interstices 44 between filaments 42. In some embodiments, filaments 42 are spaced relatively far apart. In other embodiments, filaments 42 may be spaced closely together such that securing system 20 appears to be made of a solid sheet of material or a tight mesh or netting. In some embodiments, such sheet of material may be a weave, a porous sheet or any other sheet-like material known in the art.

Figure 2:
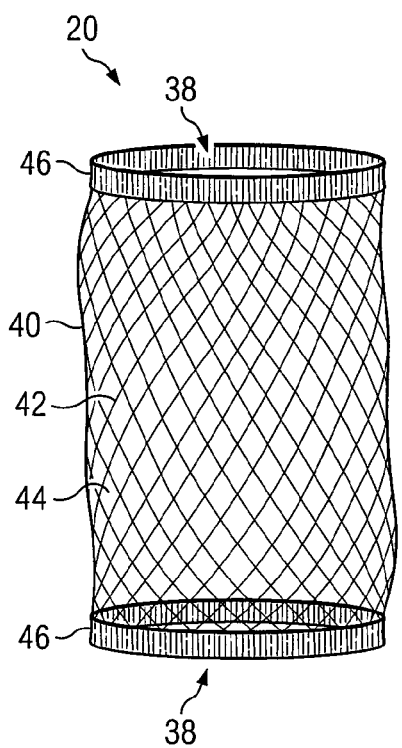
FIG. 2 illustrates a perspective view of a securing system for securing a patient interface for use with a breathing assistance system, according to one embodiment of the disclosure.

A hem 46 may be formed at each end of securing system 20. Each hem 46 may be formed from a tighter weave of elastic material or from a different elastic material than that of filaments 42. In FIG. 2, securing system 20 is shown in a relaxed or unstretched configuration.

Figure 3:
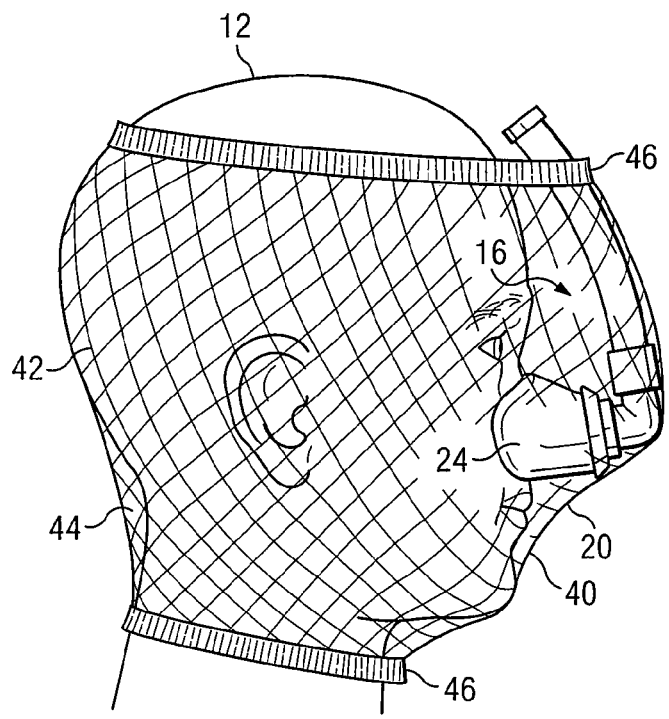
FIG. 3 illustrates a side view of a patient interface secured against a patient's face by a securing system, according to one embodiment of the disclosure.

FIG. 3 illustrates a side view of patient interface 24 secured against a patient's face by securing system 20, according to one embodiment of the disclosure. In this embodiment, mask apparatus 16 may be positioned such that patient interface 24 is positioned over the patient's nose. In other embodiments, patient interface 24 may be a mouth mask covering the patient's mouth or a face mask covering both the nose and mouth. With mask apparatus 16 in position, securing system 20 may be positioned around both mask apparatus 16 and the patient's head. As illustrated, securing system 20 may encircle the patient's head such that one hem 46 is located below the patient's jaw (e.g., restricted around the patient's neck). The opposite hem 46 may be positioned around the patient's forehead, around the crown of the patient's head, or above the top of the patient's head, for example. Filaments 42 of securing system 20, being made of elastic material, may stretch to varying degrees to relatively evenly distribute the forces necessary to secure patient interface 24 against the patient's face. Securing system 20 may substantially conform to the contours of the patient's head. As shown in FIG. 3, securing system 20 is in a stressed or stretched configuration.

Depending on the configuration of mask apparatus 16, in some embodiments it may be desirable to first place securing system 20 over mask apparatus 16 before the system is fitted to the patient's head. For example, such technique may be used where it is impossible or undesirable to disconnect mask apparatus 16 from connection system 18. In such instances, securing system 20 may be placed over mask apparatus 16 and patient interface 24 may be properly positioned against the patient's face. With patient interface 24 in position on the patient's face, securing system 20 may then be stretched and pulled down over the patient's head to the position shown in FIG. 3.

Figure 4:
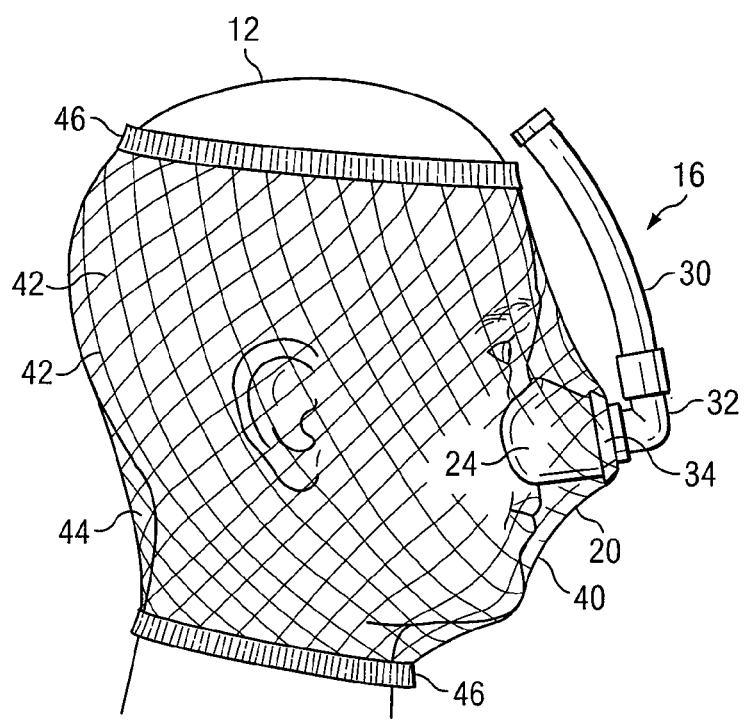
FIG. 4 illustrates a side view of a patient interface secured against a patient's face by a securing system, according to another embodiment of the disclosure.

FIG. 4 illustrates a side view of patient interface 24 secured against a patient's face by securing system 20, according to another embodiment of the disclosure. In this embodiment, portions of mask apparatus 16 (e.g., ventilation tube 30 and elbow 32) may extend through an interstice 44 or other opening formed in a wall 40 of securing system 20. In some embodiments, filaments 42 may stretch enough to allow elbow 32 to fit through the interstice 44 or opening, but not enough to allow interface coupler 34 or patient interface 24 to fit through the interstice 44 or opening. As illustrated, securing system 20 may encircle the patient's head such that one hem 46 may be below the patient's jaw (e.g., restricted around the patient's neck). The opposite hem 46 may be positioned around the patient's forehead, around the crown of the patient's head, or above the top of the patient's head. Filaments 42 of securing system 20, being made of elastic material, may stretch to varying degrees to relatively evenly distribute the forces necessary to properly secure patient interface 24 against the patient's face. Securing system 20 may substantially conform to the contours of the patient's head. As shown in FIG. 4, securing system 20 is in a stressed or stretched configuration.

In the embodiment shown in FIG. 4, securing system 20 may be stretched over interface coupler 34 or patient interface 24 to secure patient interface 24 against the patient's face. In other embodiments, securing system 20 may be fixed, secured, fastened, glued, or otherwise coupled to patient interface 24, interface coupler 34, or any other component of mask apparatus 16. For example, filaments 42 of securing system 20 may be stretched over a flange extending from patient interface 24 or interface coupler 34. As another example, filaments 42 of securing system 20 may be fixed, secured, fastened, glued, or otherwise coupled directly to patient interface 24 or interface coupler 34.

Figure 5:
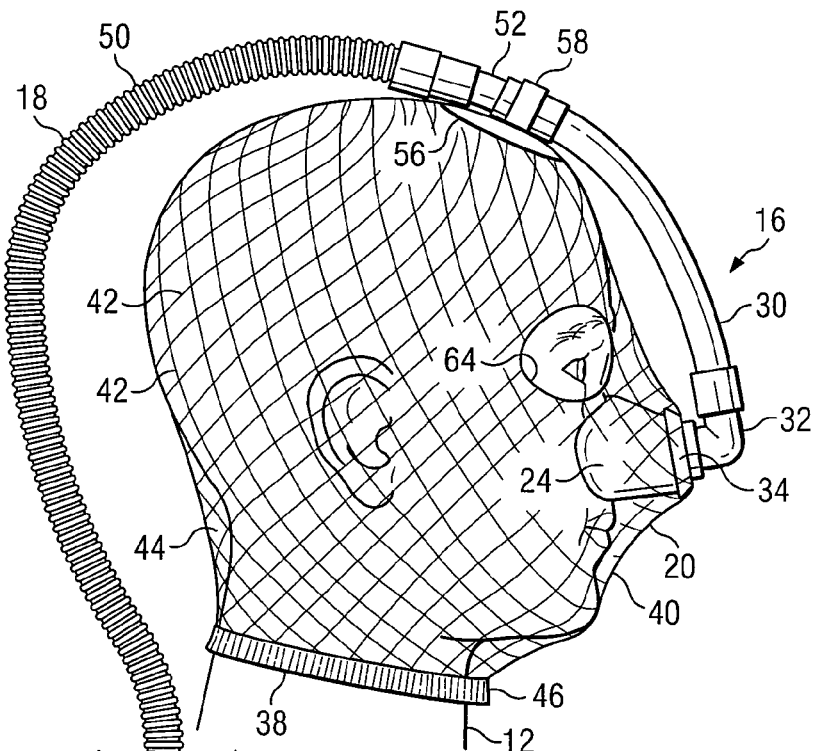
FIG. 5 illustrates a side view of a patient interface secured against a patient's face by a securing system, according to another embodiment of the disclosure.

FIG. 5 illustrates a side view of patient interface 24 secured against a patient's face by securing system 20, according to another embodiment of the disclosure. In this embodiment, a supply tube 50 of connection system 18 may be connected to ventilation tube 30 via a coupler 52. Gas delivery apparatus 14 may be configured to deliver gas to patient 12 via supply tube 50, ventilation tube 30, elbow 32, interface coupler 34, and patient interface 24.

Securing system 20 may be a hood-shaped structure substantially encircling the patient's head and having a single opening 38 at one end. Walls 40 of securing system 20 may be formed with elastic filaments 42 arranged in a criss-cross pattern forming interstices 44 between filaments 42. A hem 46 may be formed proximate opening 38. Portions of mask apparatus 16 (e.g., ventilation tube 30 and elbow 32) may extend through an interstice 44 or other opening formed in a wall 40 of securing system 20, e.g., as discussed above regarding the embodiment of FIG. 4.

Securing system 20 may include a tubing anchor 56, which may be located near the crown or top of the patient's head. Tubing anchor 56 may be formed of a tighter weave of elastic material than walls 40 or from a different elastic material than that of filaments 42. Alternatively, tubing anchor 56 may be a generally inelastic pad coupled to a wall 40 of securing system 20. A tubing wrap 58 (e.g., a pair of Velcro straps) configured to retain coupler 52 may extend from tubing anchor 56. Tubing anchor 56 and tubing wrap 58 may secure coupler 52 to filaments 42 of walls 40 of securing system 20 to maintain portions of connection system 18 in proper position relative to patient 12.

Securing system 20 illustrated in FIG. 5 may also comprise one or more eye windows 64 positioned at the patient's eyes. While some embodiments of securing system 20 may have interstices 44 wide enough for the patient to see through, filaments 42 running directly over the eyes may interfere with the patient's vision, restrict movement of the patient's eye lashes, or otherwise provide discomfort to patient 12. Eye windows 64 may allow unrestricted vision and eye movement. In some embodiments, each eye window 64 may be defined by a hem similar to hems 46 described above.

In alternative embodiments, securing system 20 may include ear windows 64 through which the patient's ears may extend. Such ear windows 64 may reduce or eliminate potential discomfort caused by filaments 42 disposed over and/or rubbing against the patient's ears. In some embodiments, each ear window 64 may be defined by a hem similar to hems 46 described above. In some embodiments, securing system may include both eye and ear window 64.

Figure 6:
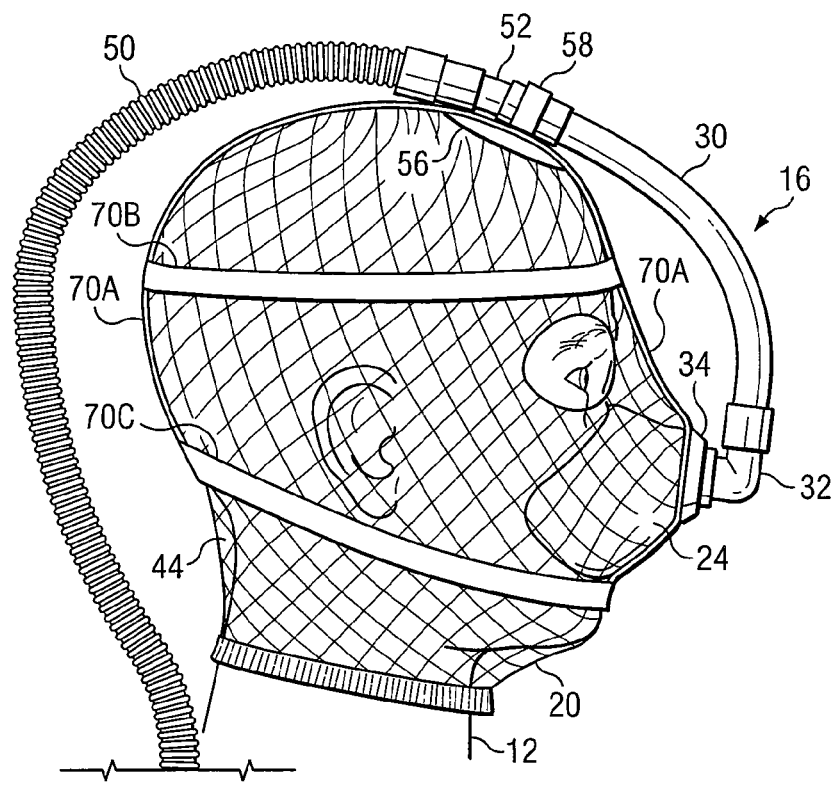
FIG. 6 illustrates a side view of a patient interface secured against a patient's face by a securing system, according to another embodiment of the disclosure.
Figure 7:
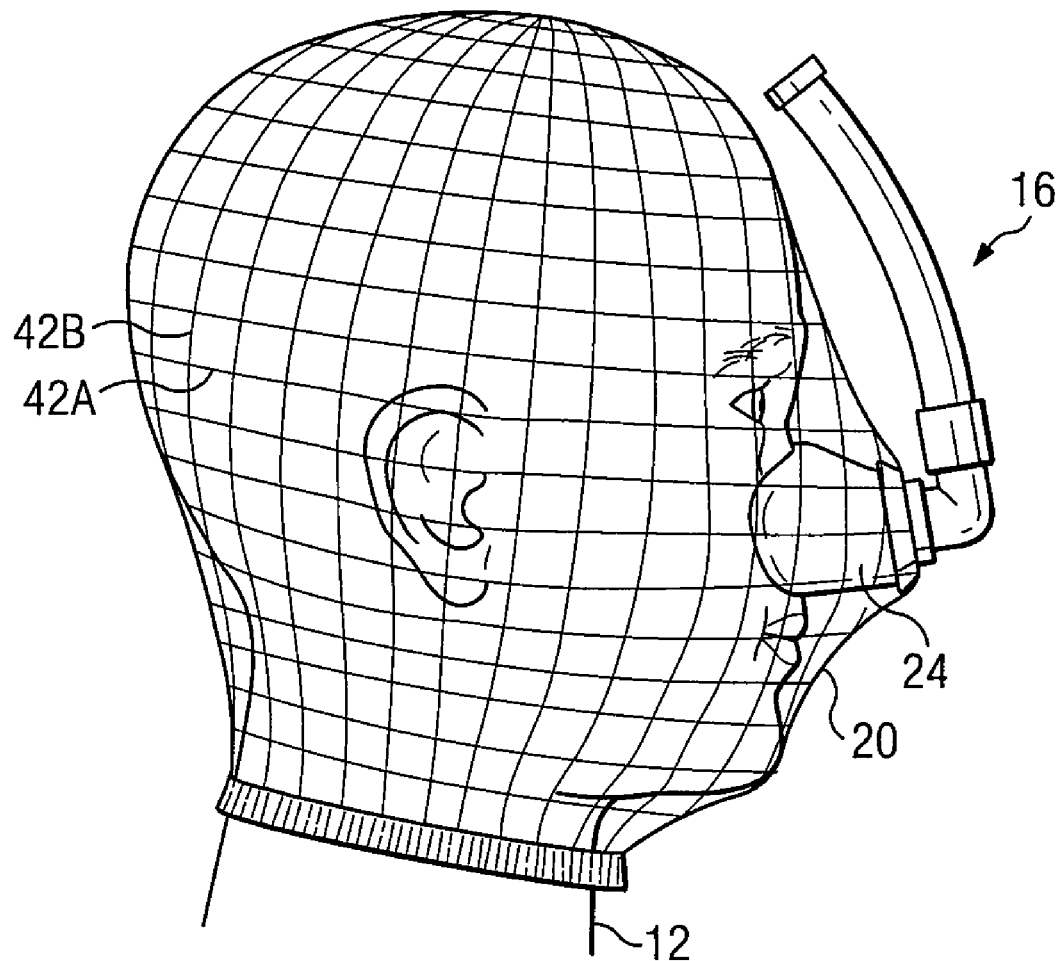
FIG. 7 illustrates a side view of a patient interface secured against a patient's face by a securing system, according to another embodiment of the disclosure.

FIG. 6 illustrates a side view of patient interface 24 secured against a patient's face by securing system 20, according to another embodiment of the disclosure. In this embodiment, patient interface 24 may cover both the patient's nose and mouth. Similar to the embodiment shown in FIG. 5, securing system 20 shown in FIG. 6 may be a hood-shaped structure having a single opening 38 at one end. Walls 40 may be formed with elastic filaments 42 arranged in a criss-cross pattern, and a hem 46 may be formed proximate opening 38. Portions of mask apparatus 16 (e.g., ventilation tube 30 and elbow 32) may extend through an interstice 44 or other opening formed in a wall 40 of securing system 20, e.g., as discussed above regarding the embodiment of FIG. 4. Similar to the embodiment shown in FIG. 5, securing system 20 shown in FIG. 6 may include a tubing anchor 56 and tubing wrap 58 for retaining coupler 52 securing coupler 52 or other portions of connection system 18 in position.

Securing system 20 of FIG. 6 may include one or more straps 70 integrated with or otherwise coupled to walls 40 of securing system 20 to provide additional support and/or structural integrity. In this illustrative configuration, a ridge strap 70A may extend from a portion of walls 40 below patient interface 24, around interface coupler 34, between the patient's eyes, and over the top of the patient's head to back of the patient's head. A brow strap 70B may extend around the patient's head proximate the brow and may connect to ridge strap 70A proximate the patient's forehead and/or at the back of the patient's head. A jaw strap 70C may extend around the patient's jaw from an area proximate patient interface 24 to the back of the patient's head. Straps 70 may be formed from any suitable elastic material, which may or may not be the same material as filaments 42.

In this embodiment, mask apparatus 16 and securing system 20 may be positioned on the patient's head by first positioning securing system 20 over mask apparatus 16. For example, patient interface 24 may be connected to interface coupler 34 and the subassembly may be placed inside the hood of securing system 20. Elbow 32 may then be inserted through ridge strap 70A at the front of the hood and connected to interface coupler 34 through securing system 20. Tubing wrap 58 may be used to secure coupler 52. Once the entire system is assembled, securing system 20 may be pulled over the patient's head until patient interface 24 is positioned over the patient's nose and mouth and hem 46 is pulled below the patient's neck. Any other suitable techniques may be used for positioning mask apparatus 16 and/or securing system 20 on the patient's head As discussed above, in some embodiments, walls 40 of securing system 20 may be formed with elastic filaments 42 arranged in a criss-cross pattern forming interstices 44 between filaments 42. Filaments 42 may be couple or arranged relative to each other to form any angles or patterns (random or non-random). In some embodiments, filaments 42 may be concentrated in areas where additional support is appropriate or desired and spaced further apart where less support is appropriate or desired. The sizes of individual filaments 42 may also vary such that larger or stronger filaments may be placed where additional support is appropriate or desired and smaller or less strong filaments may be placed where less support is appropriate or desired.

In some embodiments, filaments 42 may be configured such that securing system 20 is more elastic in some directions than others. For example, filaments 42 may be configured such that securing system 20 is generally elastic in one or more first directions and generally inelastic in one or more second directions. In the embodiment shown in FIG. 7, for example, securing system 20 may be generally elastic in radial directions but generally inelastic in the vertical direction. Securing system 20 may be generally elastic in radial directions to accommodate a variety of patient head diameters. For example, horizontally aligned filaments 42A may be generally elastic to stretch around the patient's head and patient interface 24. However, securing system 20 may be inelastic in a vertical direction such that the distance of securing system 20 from the top of the patient's head to hem 46 remains relatively constant. For example, vertically aligned filaments 42B may be generally inelastic such that their lengths remain substantially constant. Such inelasticity in the vertical direction may help maintain patient interface 24 at a proper vertical position relative to the patient's nose and/or mouth.

It will be appreciated that while the disclosure is particularly described in the context of breathing assistance systems, the apparatuses, techniques, and methods disclosed herein may be similarly applied in other contexts. Additionally, it should be understood that various changes, substitutions and alterations can be made herein without departing from the spirit and scope of the disclosure as illustrated by the following claims.

What is claimed is:

1. A breathing assistance system, comprising:
    a patient interface configured to interface with a patient to communicate gas received from a gas delivery apparatus to the patient; and
    a gas conduit system for communicating gas from the gas delivery apparatus to the patient via the patient interface;
    a securing system including a generally tubular structure open at least at one end, the generally tubular structure adapted to at least substantially cover a generally cylindrical strip of the patient's head that extends vertically between the patient's forehead and the patient's mouth and circumferentially around the patient's head, the generally tubular structure formed from mesh or netting material,
    wherein the mesh or netting material of the tubular structure covers the patient's eyes;
    wherein at least a portion of the generally tubular structure is elastic such that at least a portion of the generally tubular structure can be stretched over the patient's head; and
    wherein the securing system is configured to secure the patient interface against the patient's face.

2. A breathing assistance system according to claim 1, wherein the gas conduit system includes one or more gas conduits.

3. A breathing assistance system according to claim 1, wherein the patient interface comprises a facial cushion.

4. A breathing assistance system according to claim 1, wherein the patient interface comprises a nasal pillow.

5. A breathing assistance system according to claim 1, wherein the generally tubular structure of the securing system comprises a plurality of filaments defining interstices between adjacent filaments.

6. A breathing assistance system according to claim 1, wherein the generally tubular structure of the securing system is relatively elastic in a first direction and relatively inelastic in a second direction.

7. A breathing assistance system according to claim 1, wherein the securing system terminates at a bottom end in an elastic band or hem adapted to be positioned around the patient's neck, the elastic band or hem formed from a tighter weave of elastic material or from a different elastic material than the generally tubular structure.

8. A breathing assistance system according to claim 7, wherein the generally tubular structure of the securing system comprises a strap at least partially integrated into the generally tubular structure at a location spaced apart from the band or hem at the bottom end of the generally tubular structure.

9. A breathing assistance system according to claim 1, wherein the gas conduit system includes at least one of a ventilation tube connected to the patient interface, a connection system connected between the patient interface and the gas delivery apparatus, and a coupler for connecting the ventilation tube to the connection system.

10. A method for securing a patient interface to a patient, the method comprising:
    positioning the patient interface relative to at least one of the nose and mouth of the patient, the patient interface configured to communicate gas received from a gas delivery apparatus to the patient; and
    stretching a securing system comprising an at least partially elastic, generally tubular structure to cover a substantial portion of the patient's head, the generally tubular structure adapted to at least substantially cover a generally cylindrical strip of the patient's head that extends vertically between the patient's forehead and the patient's mouth and circumferentially around the patient's head, the generally tubular structure formed from mesh or netting material, wherein the mesh or netting material of the generally tubular structure covers the patient's eyes.

11. A method according to claim 10, wherein the positioning comprises coupling the patient interface to the gas delivery apparatus.

12. A method according to claim 10, wherein the stretching comprises lengthening filaments in the generally tubular structure of the securing system to extend the securing system around the patient's head.

13. A method according to claim 10, wherein the securing system includes a net having a plurality of filaments.

* * * * *